(12) United States Patent
Grodzins

(10) Patent No.: US 7,671,350 B2
(45) Date of Patent: Mar. 2, 2010

(54) PORTABLE X-RAY FLUORESCENCE INSTRUMENT WITH TAPERED ABSORPTION COLLAR

(75) Inventor: Lee Grodzins, Lexington, MA (US)

(73) Assignee: Thermo Niton Analyzer LLC, Billerica, MA (US)

( * ) Notice: Subject to any disclaimer, the term of this patent is extended or adjusted under 35 U.S.C. 154(b) by 0 days.

(21) Appl. No.: 12/300,790

(22) PCT Filed: May 25, 2007

(86) PCT No.: PCT/US2007/012464

§ 371 (c)(1),
(2), (4) Date: Nov. 13, 2008

(87) PCT Pub. No.: WO2008/105782

PCT Pub. Date: Sep. 4, 2008

(65) Prior Publication Data

US 2009/0220045 A1    Sep. 3, 2009

(51) Int. Cl.
G01N 23/223    (2006.01)
(52) U.S. Cl. .......... 250/515.1; 378/44; 378/45
(58) Field of Classification Search ........... 250/515.1; 378/44–50, 145
See application file for complete search history.

(56) References Cited

U.S. PATENT DOCUMENTS

| | | | |
|---|---|---|---|
| 3,353,023 A | 11/1967 | Lowery et al. | |
| 4,415,804 A | 11/1983 | Sowerby | |
| 5,740,223 A | 4/1998 | Ozawa et al. | |
| 6,256,373 B1 | 7/2001 | Bernstein et al. | |
| 6,674,087 B2 | 1/2004 | Cadwalader et al. | |
| 6,765,986 B2 | 7/2004 | Grodzins et al. | |
| 6,909,770 B2 | 6/2005 | Schramm et al. | |
| 6,965,118 B2 | 11/2005 | Martin et al. | |
| 6,965,663 B2 | 11/2005 | Ohzawa | |
| 7,020,238 B1 * | 3/2006 | Kantonen et al. | 378/44 |
| 7,443,951 B2 * | 10/2008 | Kenning et al. | 378/44 |
| 2002/0148980 A1 | 10/2002 | Cadwalader et al. | |

FOREIGN PATENT DOCUMENTS

| | | |
|---|---|---|
| EP | 0 781 992 A1 | 7/1997 |
| WO | WO 00/37928 A2 | 6/2000 |
| WO | WO 2005/010514 A1 | 2/2005 |

OTHER PUBLICATIONS

Afshari et al., "Quantitative Measurement of Lead in Paint by XRF Analysis without Manual Substrate Correction," Appl. Radiat. Isot., Elsevier Science Ltd. (Great Britain), vol. 48 (No. 10-12), pp. 1425-1431, (1997).

* cited by examiner

*Primary Examiner*—Kiet T Nguyen
(74) *Attorney, Agent, or Firm*—Charles B. Katz

(57) ABSTRACT

An instrument and method for measuring the elemental composition of a test material. The instrument has a source of penetrating radiation for irradiating an irradiated region of the test material, a detector for detecting fluorescence emission by the test material and for generating a detector signal, and a controller for converting the detector signal into a spectrum characterizing the composition of the test material. A platen of attenuating material extends outward from adjacent to, and surrounding, the irradiated surface of the test material. In certain embodiments, the thickness of the attenuating platen is tapered such as to decrease with increasing radial distance from the central irradiated region of the test material.

10 Claims, 3 Drawing Sheets

PORTABLE X-RAY FLUORESCENCE INSTRUMENT WITH TAPERED ABSORPTION COLLAR

CROSS-REFERENCE TO RELATED APPLICATIONS

This application is a National Stage application under 35 U.S.C. §371 of PCT Application No. PCT/US2007/12464, filed May 25, 2007, entitled "Portable X-Ray Fluorescence Instrument with Tapered Absorption Collar", which claims the priority benefit of U.S. application Ser. No. 11/440,570 filed May 25, 2006, entitled "Portable X-Ray Fluorescence Instrument with Tapered Absorption Collar", now U.S. Pat. No. 7,375,359, which applications are incorporated herein by reference in their entireties.

U.S. patent application Ser. No. 11/115,977, filed Apr. 27, 2005 and not yet published, and U.S. Pat. No. 6,965,118, and its priority document, Provisional Patent Application Ser. No. 60/472,674, filed May 22, 2003, are all incorporated herein by reference.

FIELD OF THE INVENTION

The invention relates methods and devices for performing x-ray fluorescence measurements while preventing exposure of personnel to dangerous levels of ambient radiation.

BACKGROUND OF THE INVENTION

X-ray fluorescence (XRF) instruments measure properties of material by irradiating the material with x-rays or gamma rays and analyzing the fluorescent radiation to determine specified properties. The term "x-rays", as used herein and in any appended claims, refers to radiation that is generated either by radioactive sources, or by instruments such as x-ray tubes, and encompasses within the term all forms of penetrating radiation including gamma rays. The specified properties to be determined may include the elemental composition of the irradiated object, or the distribution of a particular element in the near surface of the object, or the density of the object, or the morphology.

XRF instruments typically have collimated beams and appropriate shielding so that the operator is not subjected to undue ionizing radiation. For example, laboratory XRF instruments typically require the operator to completely cover the instrument and the sample so that negligible radiation emanates from the XRF instrument.

Portable XRF instruments have special radiation shielding requirements since their use typically requires that the operator hold the instrument while making the measurements. The ambient radiation levels are a primary concern. The operator and any nearby people must not be subject to undue levels of ionizing radiation. XRF instruments that inspect houses for lead paint are one specific embodiment of this invention and offer a good example of its need.

Portable XRF instruments are now the choice for quantitative determinations of the concentration of lead in painted walls of a house. Commercial portable XRF lead-paint instruments use either radioactive sources, such as $^{109}Cd$ and $^{57}Co$, or x-ray tubes, to generate the fluorescing radiation that excite the lead atoms in the painted surfaces. The intensity of the fluoresced characteristic x-rays of lead gives measure to its concentration and allows the inspector to determine whether the paint is out of compliance with established regulatory limits.

The allowable ambient radiation levels differ from country to country. The United States regulations place restrictions on the radiation levels in the ambient space directly behind the instrument's x-ray exit port. Of special concern is the space where the operator may have his hands or face. Minimal attention is paid to the radiation levels in the space between the wall being inspected and the surfaces of the operator's hands, arms and body when taking the measurements. The radiation limitations in the US can be satisfied by applying shielding in the instrument itself.

Radiation limitations in Europe are currently significantly more stringent than those in the United States. The acceptable level of radiation for an occupation worker is ten times lower; that is, 1 µSv/hr for Europe and 10 µSv/hr for the US. (µSv/hr is the standard abbreviation for microSievert per hour, a level of radiation equivalent to 100 microrem of radiation in now obsolete units.) Moreover, and of special importance to this invention, France requires that no point 10 cm from any accessible surface of the XRF instrument exceed the 1 µSv/hr level. That requirement cannot be satisfied with the shielding inside an XRF instrument.

Commercial hand-held x-ray fluorescing instruments have radiation absorbing material in the nose of the instrument. This absorbing material is designed to absorb radiation that comes directly from the source but is not going out through the exit port to strike the sample under study. This absorbing material also absorbs radiation that has been once-scattered so that the once-scattered radiation does not enter the detector and does not confound the measurement being made. The absorbing material in the nose of the inspection instrument, however, cannot prevent radiation that is multiply scattered such that it emerges from the target in a place and direction in such a way as to not intersect the nose of the instrument.

SUMMARY OF THE INVENTION

In accordance with preferred embodiments of the invention, a method is provided for inspecting a composition of a test material with a fluorescence instrument hand-held by a user. The method has steps of:

a. irradiating an irradiated region of a surface of the test material with penetrating radiation;

b. detecting fluorescent emission emitted by the test material; and c. shielding the user from ionizing radiation emitted from the surface of the test material by means of a radiation shield characterized by a thickness that decreases with radial distance from the irradiated region in a direction substantially parallel to the surface of the test material.

In accordance with another embodiment of the invention, the step of shielding the user may include shielding by means of a radiation shield extending outward from the irradiated region of the surface of the test material.

In accordance with another aspect of the invention, an instrument is provided for measuring elemental composition of a test material. The instrument has a source of penetrating radiation for irradiating an irradiated region of the test material, and a detector for detecting fluorescence emission by the test material and for generating a detector signal. The instrument also has a controller for converting the detector signal into a spectrum characterizing the composition of the test material, and a platen of attenuating material characterized by a thickness that decreases with radial distance from the irradiated region in a direction substantially parallel to the surface of the test material.

In further embodiments of the invention, the attenuating material may be a metal of atomic number greater than 45 embedded in a polymer matrix. The platen of attenuating material may be coupled to the instrument by means of fasteners, and may be detachable from the instrument, and may also include outer layers of an elastomer. The platen of attenuating material may be sized such that ionizing radiation that has interacted multiple times with the irradiated surface is attenuated by the radiation shield prior to propagation through the ambient environment. The thickness of the platen of attenuating material may decrease with radial distance from the irradiated region at a rate faster than the square of the radial distance.

BRIEF DESCRIPTION OF THE DRAWINGS

The foregoing features of the invention will be more readily understood by reference to the following detailed description, taken with reference to the accompanying drawings, in which.

DETAILED DESCRIPTION OF EMBODIMENTS

Figure 1:
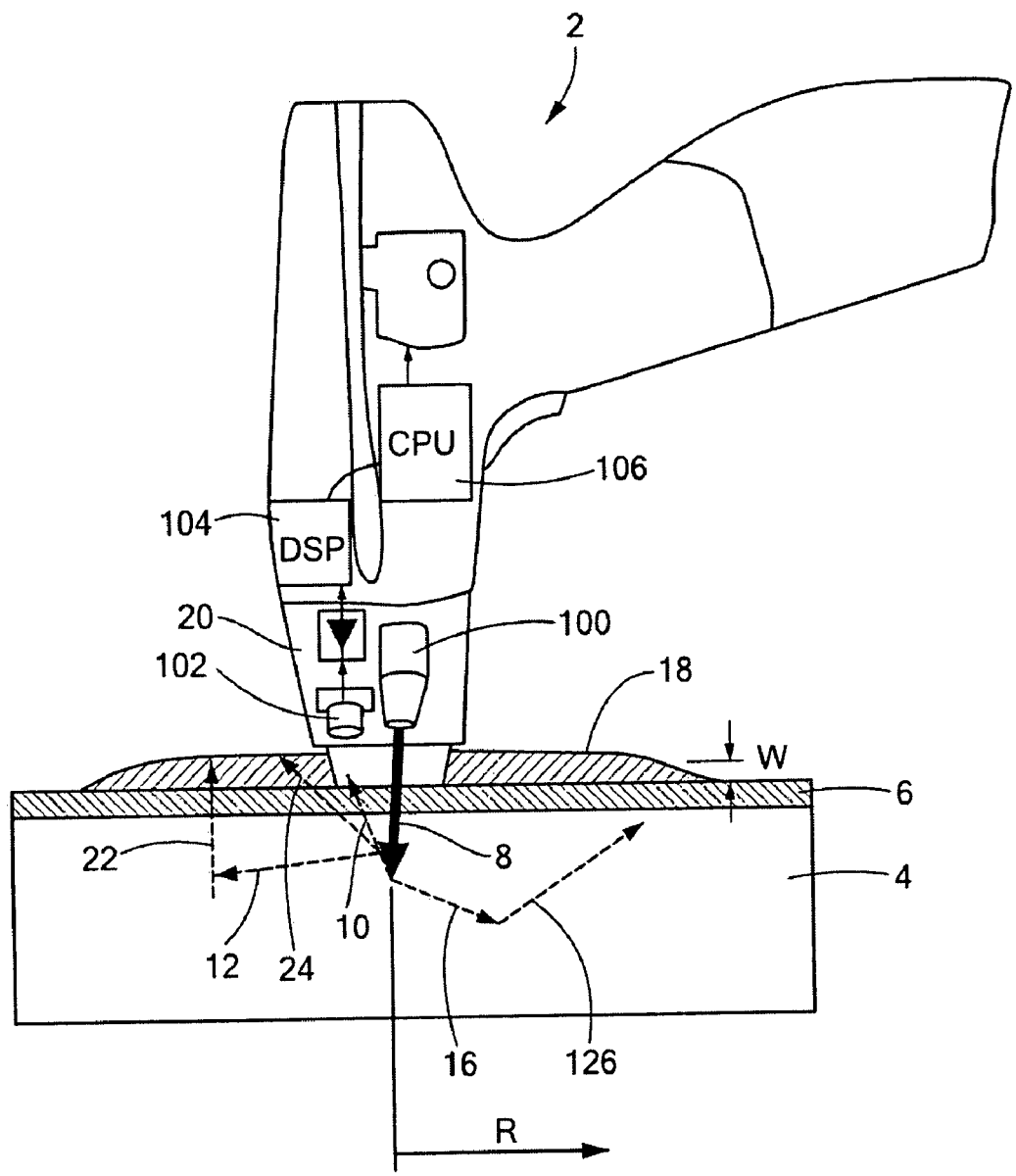
FIG. 1 is a cross-sectional view of a hand-held XRF instrument with a tapered radiation shield for protecting the user from ionizing radiation that emanates from the test sample, in accordance with an embodiment of the present invention.

In accordance with embodiments of the present invention, and as described now with reference to FIG. 1, shielding in the form of a collar is used to prevent multiple scattered x-rays from exiting the wall relatively far from the XRF instrument with sufficient intensity to exceed regulatory limits.

To fully appreciate why the present invention is needed and how it must be designed we need to understand the origin of the ambient radiations that result when a beam of x-rays enters material and gets Compton scattered.

The Physics of Ambient Radiation

The following discussion refers particularly to an XRF instrument used for lead paint analysis, however it should be appreciated that the conclusions drawn, and the invention described, are applicable to a wide group of applications, especially the XRF analysis of soils and plastics.

The energies of the x-rays that fluoresce lead are typically in the 20 keV range when the L x-rays of lead at 10.5 keV and 12.6 keV are used for the analysis, and above 88 keV when the K x-ray lines, at 72.8 keV and 75 keV, are used for the analysis. In the following description we will restrict ourselves to fluorescing energies of 22.2 keV (from $^{109}$Cd) used to excite the L lines, and 122 keV (from $^{57}$Co) used to excite the K lines. It is to be understood, however, that these particulars are presented by way of illustration and not by way of limitation.

Referring to FIG. 1, a hand-held XRF instrument 2 is depicted in a position abutting a wall 4. Instrument 2 emits penetrating radiation predominantly along a propagation axis designated by arrow 8 (which numeral also designates the emitted x-rays) and will be discussed herein as an XRF instrument 2 that emits x-rays 8. X-rays 8 are generated by source 100, which may be a radioactive source, as shown, or an x-ray tube, or other x-ray generating device. X-rays 8 exit from the XRF instrument 2, and enter a test sample 6, which, in the example depicted, is a paint layer on wall 4. Some of the x-rays 8 give rise to fluorescence 10, or scattering, back into the instrument 2 to either be counted in the detector 102 of XRF instrument 2 or absorbed by the walls 20 of the instrument. Detection of fluorescence photons gives rise to a detector signal which is processed by digital signal processor 104 and controller 106 to produce a spectrum that provides for identification of the elemental content of the test sample 6 in accordance with techniques described, for example, in U.S. Pat. No. 6,765,986, (to Grodzins et al., issued Jul. 20, 2004), which is incorporated herein by reference.

Some of the x-rays 24, scatter backwards out of the wall, and miss the XRF instrument. Many x-rays, 12 and 16, however, scatter into the wall material itself. And some of those that scatter into the wall material scatter again resulting in x-rays 22 and 126 that exit the painted wall at a considerable distance from the XRF instrument 2.

The relative intensity of the x-rays that exit the wall in this way depends on the angular distributions of the Compton scattering, the energies of the scattered radiations and the distances the scattered radiations travel in the material of the wall between interactions. As we describe below, the scattering is, within a factor of about 2, isotropic; the energy of the scattered x-rays are almost as high as the incident energy; and the distance that the x-ray cascade travels in the wood before dissipating can be many centimeters. Therefore, shielding, as described herein, is desirable to reduce the levels of radiation to which a user is exposed to within specified safety levels, such as those enumerated above.

The angular distributions of Compton scattering for the x-rays of interest in XRF are similar to the distributions of Thompson (classical) scattering. The probability of Thompson scattering through an angle θ is proportional to $(1+\cos^2 \theta)$. The intensity of backscattering is equal to that of forward scattering and side scattering is half as strong. The scattering of 22 keV x-rays follows the Thompson formula within a few percent. The Compton scattering of 122 keV x-rays is more forward peaked but side scatter and back scatter remain very probable.

The change in the energy of the x-rays when scattered through a particular angle θ depends strongly on the x-ray energy. A 22 keV x-ray scattered through 90° only loses 1 keV to the scattering electron so that the scattered x-rays has 21 keV. A 122 keV x-ray scattered through 90° loses about 24 keV and ends up being 98 keV.

The distance that the x-rays travel in the wall medium depends strongly on the composition of the medium. It is useful to measure that distance in mean free paths (MFP). The mean free path for an incident x-ray is the distance a beam of the x-rays will travel in the medium before the intensity of the incident x-ray has dropped by a factor of 2.718. The intensity of the incident beam may drop because x-rays have been absorbed by the photo-electric effect, in which case the x-rays will not contribute to ambient radiation.

The photoelectric effect results in secondary x-rays generated when the photoelectric excited atom relaxes to its ground state. These characteristic x-rays can be intensive enough in special circumstances to add significantly to the ambient radiation. These secondary x-rays may also advantageously be absorbed by the radiation shield that is described herein. Additionally, radiation shield 18 may also advantageously block singly scattered x-rays such as those designated by numeral 24.

If the intensity of the incident beam drops because of scattering, then the incident x-ray has simply been transformed into a lower energy x-ray traveling in a new direction and it can still contribute to ambient radiation.

Table 1 gives the mean free paths of the 22 keV and the 122 keV x-rays, and the energies of the x-rays of 21 keV and 98 keV after a 90° scattering. The materials are air, wood, plaster, aluminum, and iron.

TABLE 1

Mean Free Paths in Centimeters

|  | 22 keV | 21 keV | 122 keV | 98 keV |
|---|---|---|---|---|
| air | 1756 | 1592 | 5455 | 5162 |
| wood | 3.59 | 3.26 | 11.11 | 10.55 |
| brick | 0.28 | 0.24 | 3.42 | 3.13 |
| aluminum | 0.15 | 0.13 | 2.59 | 2.33 |
| iron | 0.07 | 0.06 | 0.54 | 0.36 |

The mean free paths for 22 keV radiations are many meters in air, several centimeters in wood and several millimeters or less in heavy materials that make up common walls. The 122 keV radiations used to excite the K lines of lead go several to many centimeters in all common wall material but steel.

Table 2, which gives the probability that an x-ray will be scattered at least once in traversing the material before being absorbed gives further insight into what is happening.

TABLE 2

Probability that the X-ray will be Scattered at Least Once

|  | 22 keV | 21 keV | 122 keV | 98 keV |
|---|---|---|---|---|
| air | 40% | 33% | 99.6% | 98.6% |
| wood | 40% | 33% | 99.3% | 98.5% |
| brick | 8% | 7% | 95% | 91% |
| aluminum | 6% | 5% | 93% | 87.5% |
| iron | 0.6% | 0.5% | 52% | 38% |

From Table 1 it is apparent that any 22 keV x-rays that pass through the paint 6 into the wooden wall 4 will travel several centimeters before interacting. And when a 22 keV x-ray does interact, there is 40% probability that the x-ray will scatter and not be absorbed. Furthermore, there is a strong probability that the scattering will be to side. Those side-scattered x-rays will have almost the same energy as the incident energy and will themselves travel several centimeters before interacting. And again the probability of scattering is high. It is easy to see that a significant amount of radiation can escape from the wood 4 on the sides of the XRF instrument 2.

Materials with higher atomic number and greater density than wood present much less of a problem because, as Table 1 and Table 2 show, the x-rays do not travel far in these materials and they quickly get absorbed.

Table 1 and Table 2 also show why K-shell XRF analyzers that measure the lead concentration by studying the K lines have a far more difficult time controlling the ambient radiation. Scattering completely dominates over absorption except for steel walls and the scattered radiations can travel 10 cm in wood before interacting.

One embodiment of a radiation shield is the tapered platen designated by numeral 18, shown in FIG. 1. The weight of the radiation shield (or collar) 18 may be advantageously minimized by taking into account that the needed absorption thickness decreases with the radius R of the collar; i.e. the distance from the x-ray beam entry point. The verb "taper," and cognate terms, as used herein, refers to a substantially monotonic decrease of platen width with distance from the target spot, whether in a continuous or stepped manner, and without regard to the functional form of the decrease.

Figure 2:
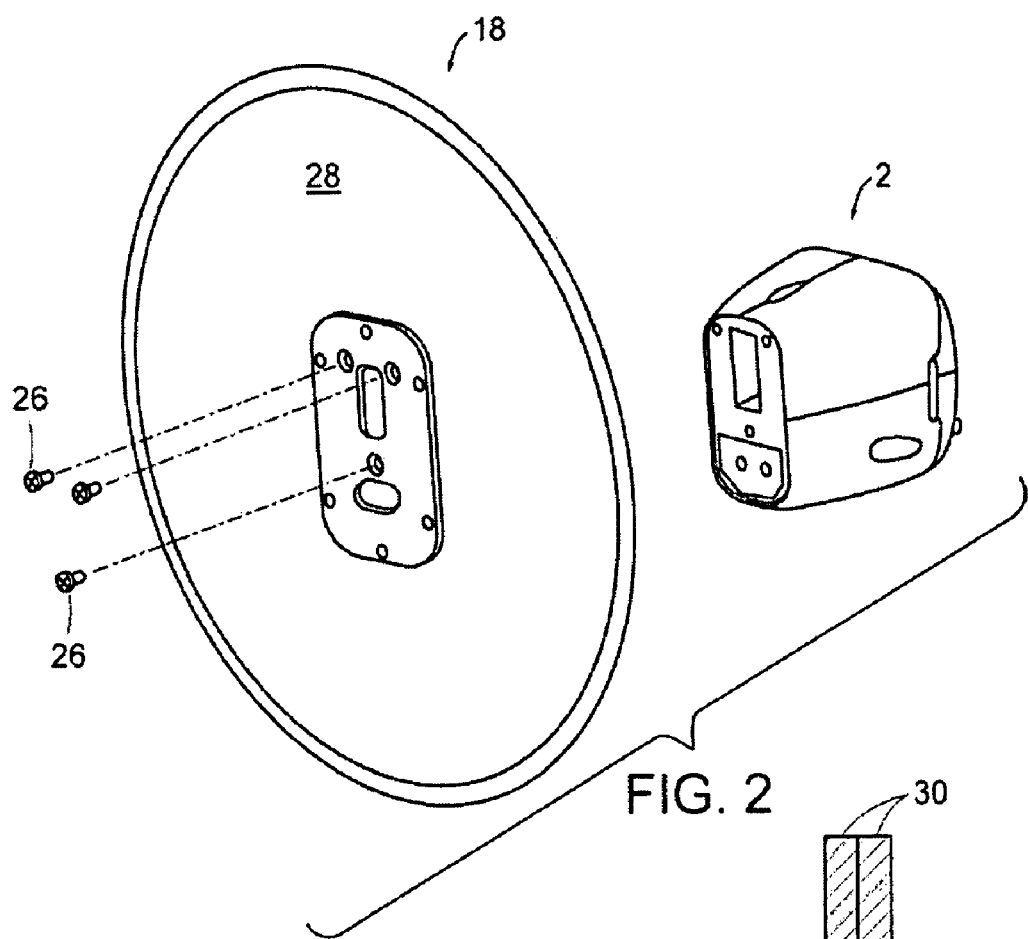
FIG. 2 is a perspective view of a radiation shield, in accordance with an embodiment of the present invention, depicting, in an exploded format, its attachment to an XRF instrument.

A collar 18 of parallel surfaces, described below with reference to FIG. 2, is a uniform disc of rubber (or other elastomer) filled with tungsten (or other element of atomic number typically greater than 45), and works well up to at least 50 keV.

Performance of collar 18 becomes more critical as the x-ray energy gets into the 100 keV range where, especially in light-element materials, the x-rays must suffer several to many Compton scatterings before getting stopped by absorption via photo electric interactions in the test sample. A simple calculation based on a 1 watt beam of 100 keV electrons striking a tungsten anode indicates that the collar may have to be at least 10 mean free paths thick at radial distances of a few inches.

In general, the collar diameter and the absorption must increase as the energy of the primary x-ray beam increases. As the x-ray energy increases, the weight of a collar of uniform thickness (based on the absorption needed at small radii) begins to be a significant fraction of the total weight of a hand-held instrument, and, being in the front of the instrument, a significant burden on the operator.

Consequently, in accordance with preferred embodiments of the invention, collar 18 is characterized by a thickness w that varies as a function of radius R (i.e., distance from the x-ray entry point, or the irradiated region of the test sample, to the extent that the irradiated region is more properly characterized as an area rather than a point). Tapering of thickness w advantageously provides for optimizing the cross-section of collar 18 for minimum weight. Collar 18 is tapered, becoming thinner towards the outer perimeter since the number of x-rays and the mean energy of the x-rays that must be shielded decrease with distance from the entrance point of the initiating x-ray beam.

In order to understand the desirability of a tapered profile, one may consider a ring of target wall 4. Because of absorption, the number of x-rays exiting per cm of wall, falls faster than the square of the radius measured from the point the x-ray beam enters the target wall.

In the hypothetical case of no absorption of the x-rays traveling in the wall, there will be the same number of x-rays passing through each successive ring from the center point. The number of x-rays per square cm (and hence the number of x-rays scattered out of the wall) will decrease as the square of the radius, so that the collar thickness w, assumed for the sake of simplicity to be against the wall 4, can decrease with radius R. (The absorber thickness can decrease by log 4 (i.e. 40%) for every factor of 2 greater radial distance.)

Since wall 4 does absorb x-rays, by scattering and photoelectric interactions, the number of x-rays emanating from successive rings from the center will decrease faster than the square of the radius. Moreover, considering multiple scattering, each successive scatter decreases the x-ray energy so that the mean energy of the exiting x-rays also falls as a function of radius. Thus, the necessary thickness of absorption collar 18 can decrease rapidly with radius so that the weight of the tapered (or feathered) collar is advantageously significantly less than the weight of a collar of uniform thickness.

Radiation shield 18, in accordance with another embodiment of the invention, is shown in perspective view in FIG. 2. Radiation shield 18 is coupled to XRF instrument 2 by fasteners 26 which may include screw, rivets, clips, or any other fasteners. Radiation shield 18 may be readily detachable or exchangeable.

Figure 3:
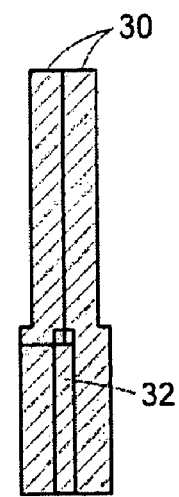
FIG. 3 is a cross-section of a radius of the radiation shield of FIG. 2, showing the a laminated shield structure.

In certain embodiments of the invention, radiation shield 18 has a platen 28 of shielding material, shown in cross-section in FIG. 3. The platen may be referred to herein as a 'membrane'. In a preferred embodiment, platen 28 is circular, and has a diameter of approximately 20 cm. Other shapes and sizes are within the scope of the present invention, for example, radiation shield 18 may extend outward conically from the propagation axis 8 (shown in FIG. 1). FIG. 3 shows a laminate formed of two layers of elastomer (such as rubber) with an included layer 32 of shielding material, such as a metal of high atomic number, typically greater than Z=45, embedded in a polymer matrix. Such metals may include tin, tungsten or lead. A preferred material is tungsten-filled polyvinyl chloride (PVC). The platen is preferably flexible to allow it to conform to contours of the abutted surface, such as to measure as close as possible to a corner, or to interrogate a niche in a wall such as the slide recess for a window.

Figure 4:
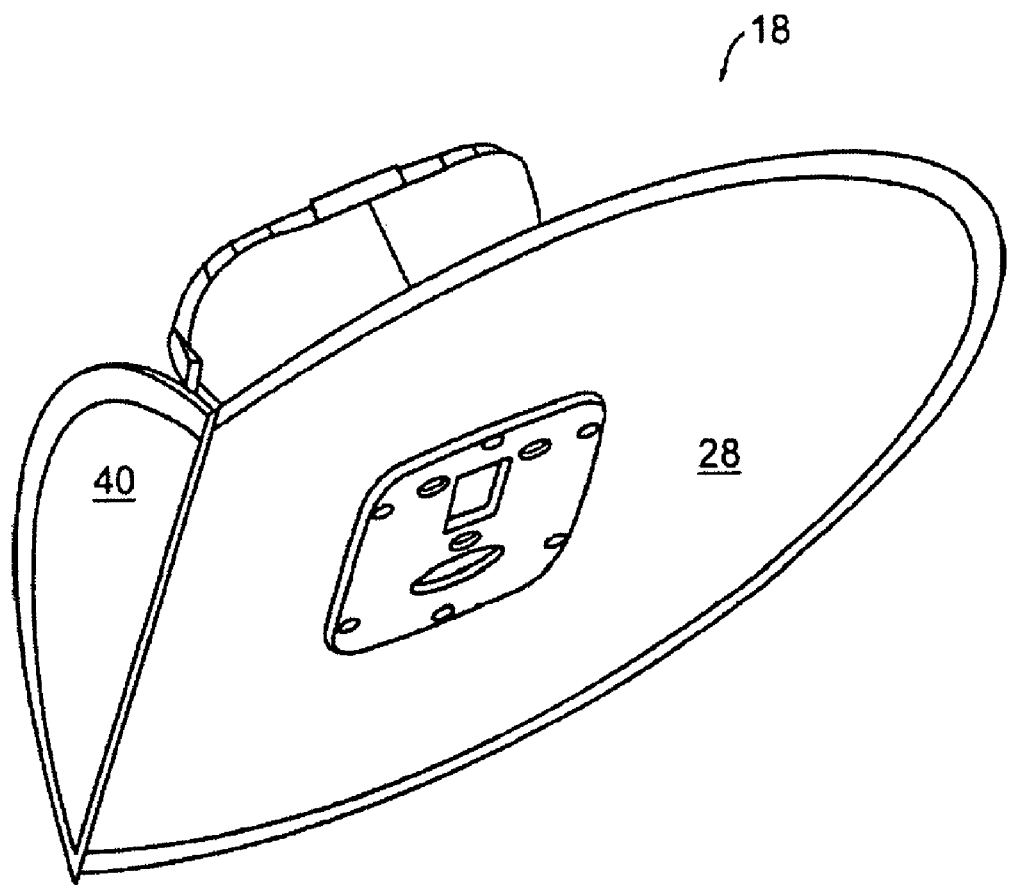
FIG. 4 is a perspective view from beneath of a radiation shield allowing for use of an XRF instrument in a corner.

In accordance with other embodiments of the invention, referring now to FIG. 4, a section 40 of radiation shield 18 may lie in a plane other than the major part of platen 28 in order to allow the radiation shield to be used, for example, in inside corners of walls. Non-coplanar section 40 may be coupled to the rest of platen 28 at a fixed bend, or, alternatively, by a hinge, all as well-known in the art.

The described embodiments of the invention are intended to be merely exemplary and numerous variations and modifications will be apparent to those skilled in the art. All such variations and modifications are intended to be within the scope of the present invention as defined in the appended claims.

What is claimed is:

1. A handheld x-ray fluorescence instrument for measuring elemental composition of a test material, the instrument comprising:
   a. a source of x-ray radiation for irradiating an irradiated region of the test material;
   b. a detector for detecting fluorescence emission by the test material and responsively generating a detector signal;
   c. a controller for converting the detector signal into a spectrum characterizing the composition of the test material; and
   d. a radiation shield extending outwardly from a nose of the instrument, the radiation shield being fabricated from a flexible material such that the nose may be brought into close proximity to a surface of the test material.

2. An instrument in accordance with claim 1, wherein the flexible material is a polymer matrix having a radiation attenuating substance embedded therein.

3. An instrument in accordance with claim 2, wherein the radiation attenuating substance is a metal of atomic number greater than 45.

4. An instrument in accordance with claim 1, wherein the radiation shield is detachable from the instrument.

5. An instrument in accordance with claim 1, wherein the radiation shield comprises a layer of attenuating material disposed between outer layers of an elastomer.

6. An instrument in accordance with claim 1, wherein the radiation shield is sized such that ionizing radiation that has interacted multiple times with the irradiated surface is attenuated by the radiation shield prior to propagation through the ambient environment.

7. An instrument in accordance with claim 1, wherein the radiation shield is characterized by a thickness that decreases with radial distance from the irradiated region.

8. An instrument in accordance with claim 7, wherein the radiation shield is characterized by a thickness that decreases with radial distance from the irradiated region at a rate faster than the square of the radial distance.

9. An instrument in accordance with claim 1, wherein the radiation shield extends outwardly and forwardly from the nose of the instrument.

10. An instrument in accordance with claim 9, wherein the radiation shield has a generally frustro-conical shape.

* * * * *